(12) United States Patent
Roush et al.

(10) Patent No.: US 8,968,213 B2
(45) Date of Patent: Mar. 3, 2015

(54) CYTOLOGY BRUSH APPARATUS WITH IMPROVEMENTS

(75) Inventors: Eric Roush, Cleveland Heights, OH (US); Christopher J. Kaye, Concord, OH (US)

(73) Assignee: United States Endoscopy Group, Inc., Mentor, OH (US)

(*) Notice: Subject to any disclaimer, the term of this patent is extended or adjusted under 35 U.S.C. 154(b) by 17 days.

(21) Appl. No.: 13/276,028

(22) Filed: Oct. 18, 2011

(65) Prior Publication Data

US 2014/0088459 A1  Mar. 27, 2014

Related U.S. Application Data

(60) Provisional application No. 61/394,400, filed on Oct. 19, 2010.

(51) Int. Cl.
  *A61B 10/02* (2006.01)
  *A61M 25/00* (2006.01)
  *A61B 10/04* (2006.01)

(52) U.S. Cl.
  CPC ............ *A61M 25/0032* (2013.01); *A61B 10/04* (2013.01)
  USPC ........................................ 600/569

(58) Field of Classification Search
  USPC ........................................ 600/569
  See application file for complete search history.

(56) References Cited

U.S. PATENT DOCUMENTS

| | | |
|---|---|---|
| 1,425,435 A | 8/1922 | Allen |
| 1,711,352 A | 4/1929 | Jeffreys |
| 2,701,559 A | 2/1955 | Cooper |
| 2,739,585 A | 3/1956 | Ayre |
| 2,839,049 A | 6/1958 | MacLean |
| 2,847,990 A | 8/1958 | Ayre |
| 2,955,591 A | 10/1960 | MacLean |
| 3,074,396 A | 1/1963 | MacLean |
| 3,513,830 A | 5/1970 | Kalayjian |
| 3,613,664 A | 10/1971 | Willson et al. |
| 3,800,781 A | 4/1974 | Zalucki |

(Continued)

OTHER PUBLICATIONS

Boon, Mathilde E. et al., Exploiting the "Toothpick Effect" of the Cytobrush by Plastic Embedding of Cervical Samples, The International Academy of Cytology, Jan.-Feb. 1991, pp. 57-63, Science Printers and Publishers, St. Louis MO.

(Continued)

*Primary Examiner* — Sean Dougherty
*Assistant Examiner* — Michael C Stout
(74) *Attorney, Agent, or Firm* — Calfee, Halter & Griswold LLP (57) ABSTRACT

A tissue collection apparatus maximizes the collection and retention of tissue samples from within a patient. The apparatus comprises a handle with a hollow catheter flexibly extending distally from the handle. A cytology brush is stored within the hollow at a distal end of the cannula, and can be extended and retracted from the cannula by manipulating the handle. The cytology brush has a cylindrical proximal brush, a cylindrical distal brush, and a tissue collection gap longitudinally separating the proximal and distal brushes. The bristles of the brushes can have different material properties and can have an effective diameter greater than the cannula. In use, tissue samples accumulate within the bristles and within the tissue collection gap. When retracted into the hollow of the cannula, the apparatus maximizes the amount of tissue collected by folding the bristles over the tissue collection gap to shield the tissue samples collected within.

18 Claims, 6 Drawing Sheets

(56) References Cited

U.S. PATENT DOCUMENTS

| | | | |
|---|---|---|---|
| 3,881,464 A | 5/1975 | Levene | |
| 4,108,162 A | 8/1978 | Chikashige et al. | |
| 4,136,680 A | 1/1979 | Southworth | |
| 4,227,537 A | 10/1980 | Suciu et al. | |
| 4,235,244 A | 11/1980 | Abele et al. | |
| 4,235,245 A | 11/1980 | Naito | |
| 4,243,049 A | 1/1981 | Goodale et al. | |
| 4,361,948 A | 12/1982 | Omata | |
| 4,465,072 A | 8/1984 | Taheri | |
| 4,759,376 A | 7/1988 | Stormby | |
| 4,763,670 A | 8/1988 | Manzo | |
| 4,877,037 A | 10/1989 | Ko et al. | |
| 4,936,312 A | 6/1990 | Tsukagoshi | |
| 4,966,162 A | 10/1990 | Wang | |
| 5,022,408 A | 6/1991 | Mohajer | |
| 5,056,529 A | 10/1991 | de Groot | |
| 5,146,928 A | 9/1992 | Esser | |
| 5,217,023 A | 6/1993 | Langdon | |
| 5,427,115 A | 6/1995 | Rowland et al. | |
| 5,456,265 A | 10/1995 | Yim | |
| 5,474,075 A | 12/1995 | Goldberg et al. | |
| 5,535,756 A | 7/1996 | Parasher | |
| 5,578,018 A | 11/1996 | Rowland et al. | |
| 5,615,439 A * | 4/1997 | Bourrelly | 15/104.2 |
| 5,681,335 A | 10/1997 | Serra et al. | |
| 5,713,369 A * | 2/1998 | Tao et al. | 600/569 |
| 5,722,423 A | 3/1998 | Lind et al. | |
| 5,738,109 A | 4/1998 | Parasher | |
| 5,876,138 A * | 3/1999 | Gueret | 401/129 |
| 5,882,329 A | 3/1999 | Patterson et al. | |
| 5,899,850 A | 5/1999 | Ouchi | |
| 5,902,263 A | 5/1999 | Patterson et al. | |
| 6,022,363 A | 2/2000 | Walker et al. | |
| 6,030,397 A * | 2/2000 | Monetti et al. | 606/159 |
| 6,066,152 A | 5/2000 | Strauss et al. | |
| 6,193,674 B1 | 2/2001 | Zwart | |
| 6,297,044 B1 | 10/2001 | Eisen et al. | |
| 6,676,609 B1 | 1/2004 | Rutenberg et al. | |
| 7,004,913 B1 | 2/2006 | Rutenberg et al. | |
| 7,416,555 B2 | 8/2008 | Krivoruchko | |
| 7,722,613 B2 * | 5/2010 | Sutterlin et al. | 606/79 |
| 8,021,380 B2 * | 9/2011 | Thompson et al. | 606/159 |
| 2001/0046406 A1 * | 11/2001 | Schrepf | 401/126 |
| 2004/0260199 A1 | 12/2004 | Hardia, Jr. et al. | |
| 2006/0287667 A1 * | 12/2006 | Abela | 606/200 |
| 2007/0198028 A1 * | 8/2007 | Miloslavski et al. | 606/127 |
| 2009/0182362 A1 * | 7/2009 | Thompson et al. | 606/159 |
| 2009/0306702 A1 * | 12/2009 | Miloslavski et al. | 606/200 |
| 2010/0234848 A1 * | 9/2010 | Sutterlin et al. | 606/79 |
| 2010/0307223 A1 * | 12/2010 | Jeftic-Stojanovski et al. | 73/12.04 |

OTHER PUBLICATIONS

Lonky, Neal et al., Comparison of Standard Papanicolaou Smears and Directed Cytologic Sampling Guided by Speculoscopy, International Journal of Gynecology & Obstetrics, XIV World Congress of Gynecology and Obstetrics (FIGO) 1994, Society of Obstetricians and Gynaecologists of Canada.

Cover letter, trademark application for the mark SPIRABRUSH CX, signed Declaration and Power of Attorney, photograph of the submitted "SpiraBrush" sample, First Used in Interstate Commerce Dec. 4, 1992.

\* cited by examiner

CYTOLOGY BRUSH APPARATUS WITH IMPROVEMENTS

CROSS REFERENCE TO RELATED APPLICATIONS

The present application hereby claims the benefit of the provisional patent application of the same title, Ser. No. 61/394,440 filed on Oct. 19, 2010, the disclosure of which is hereby incorporated by reference in its entirety.

FIELD OF THE APPARATUS

The present embodied apparatus relates, in general, to a device for tissue acquisition, and more particularly, pertains to a tissue removing scraper, rasp or cytology brush for the collection of microbiological biopsy or tissue specimen from a body cavity such as the upper and lower gastro-intestinal systems or the biliary tract.

BACKGROUND

The analysis of cell samples is a valuable tool in the treatment of disease. If a patient complains of an issue with their body, or portion of tissue appears unusual in appearance, it is common practice to obtain a sample of the cells at that site, and to analyze the sample in a lab. If the tissue is hard, such as that found with a hard tumor, a biopsy coring needle or a rasp or a scraper can be used. If the surgical site is softer tissue such as the mucosal or submucosal tissue found within the gastrointestinal tract, a scraper, rasp or cytology brush can be used.

Cytology brushes are well known in the art, and have been available to the medical community for a very long time. Flexible shafts were added to the cytology brushes to increase access to hard to reach portions of the patient. With the advent of endoscopic surgery, cytology brushes were adapted for endoscopic use. As endoscopes advanced, more and more hard-to-reach areas became available for cytological brush sampling. Today, flexible shaft cytology brushes can be used during endoscopic surgery to access difficult-to-reach portions of the patient's anatomy. Tissue samples can now be taken with a cytology brush from within the difficult-to-access biliary tract, which can be of great help in the early diagnosis of diseases of the gall bladder and pancreas.

Consequently, a significant need exists for an improved cytology brush apparatus that can access difficult-to-reach anatomy, and provide improved cell collection at the surgical site.

BRIEF SUMMARY

The apparatus overcomes the above-noted and other deficiencies of the prior art by providing an apparatus for the collection and retention of tissue samples from within a patient. An apparatus for the collection and retention of tissue samples from within a patient comprises a handle with a flexible cannula extending distally from the handle. A first inner lumen extends along the apparatus from the handle to a distal end of the cannula. The first inner lumen also has an inner surface and a distal lumen opening at a distal end of the cannula. A brush is provided for collecting tissue samples. The brush is movable in and out of the distal lumen opening in response to actuation of the handle. The brush comprises a shaft extending from the inner lumen to define a longitudinal axis extending through the shaft to the handle. A proximal portion of bristles extends cylindrically from the shaft and a distal portion of bristles extends cylindrically from the shaft. A tissue collector is located between the proximal portion of bristles and the distal portion of bristles. The tissue collector is configured to collect tissue samples within, and to retain the tissue samples as the brush is moved into the distal lumen opening of the cannula.

Alternately, an apparatus for the collection and retention of tissue samples from within a patient is disclosed by providing a handle and a flexible cannula extending distally from the handle. The flexible cannula further comprises a first lumen within that extends from the handle to a distal end of the cannula with a distal lumen opening within the distal end. A cytology brush extends from the first lumen at a distal end of the flexible cannula. The cytology brush is configured to collect and store tissue samples, and further configured to move from the extended position to a retracted position within the lumen in response to actuation of the handle. The movable cytology brush comprises a shaft extending longitudinally along a longitudinal axis that extends from the cytology brush to the handle and a proximal brush portion comprising a cylindrical array of bristles extending from the shaft. A central brush portion is located distal to the proximal brush portion and comprises a cylindrical array of bristles extending from the shaft. A distal brush portion is located distal to the central brush portion and comprises a cylindrical array of extending from the shaft. A first tissue collector is located between the proximal and the central brush portions, and a second tissue collector is located between the central and the distal brush portions. Wherein the bristles are operably configured to expand away from the shaft when the brush is in the extended position, and to fold when moved into the retracted position within the first lumen. And when the brush has collected tissue samples from the patient, the tissue collectors and bristles are operably configured to protect tissue samples therein from being removed as the brush moves into the retracted position within the lumen.

And, alternately, a method of collecting and retaining tissue samples from within a patient is disclosed. The method comprising the first step of providing a cytology brush apparatus having a longitudinal axis and a hollow flexible cannula extending along the longitudinal axis. A longitudinally movable cytology brush extends from a distal end of the hollow within the flexible cannula. The cytology brush comprises a proximal bristle portion, a distal bristle portion, and a first tissue collector between the proximal bristle portion and the distal bristle portion. A second step is provided to collect tissue samples within the bristles and tissue collector of the cytology brush at a surgical site within the patient. A third step is provided to draw the extended cytology brush and collected tissue samples into the hollow of the flexible cannula. A fourth step is provided of retaining the tissue sample collected within the tissue collector by folding bristles across the first tissue collector as the extended cytology brush and collected tissue samples are drawn into the hollow.

These and other objects and advantages of the present apparatus and the method of use thereof shall be made apparent from the accompanying drawings and the description thereof.

BRIEF DESCRIPTION OF THE FIGURES

The accompanying drawings, which are incorporated in and constitute a part of this specification, illustrate embodiments of the apparatus, and, together with the general description of the apparatus given above, and the detailed description of the embodiments given below, serve to explain the principles of the present apparatus.

DETAILED DESCRIPTION

The following description of certain examples of the apparatus should not be used to limit the scope of the present apparatus. Other examples, features, aspects, embodiments, and advantages of the apparatus will become apparent to those skilled in the art from the following description, which is by way of illustration, one of the best modes contemplated for carrying out the apparatus. As will be realized, the apparatus is capable of other different and obvious aspects, all without departing from the spirit of the apparatus. Accordingly, the drawings and descriptions should be regarded as illustrative in nature and not restrictive.

Figure 1:
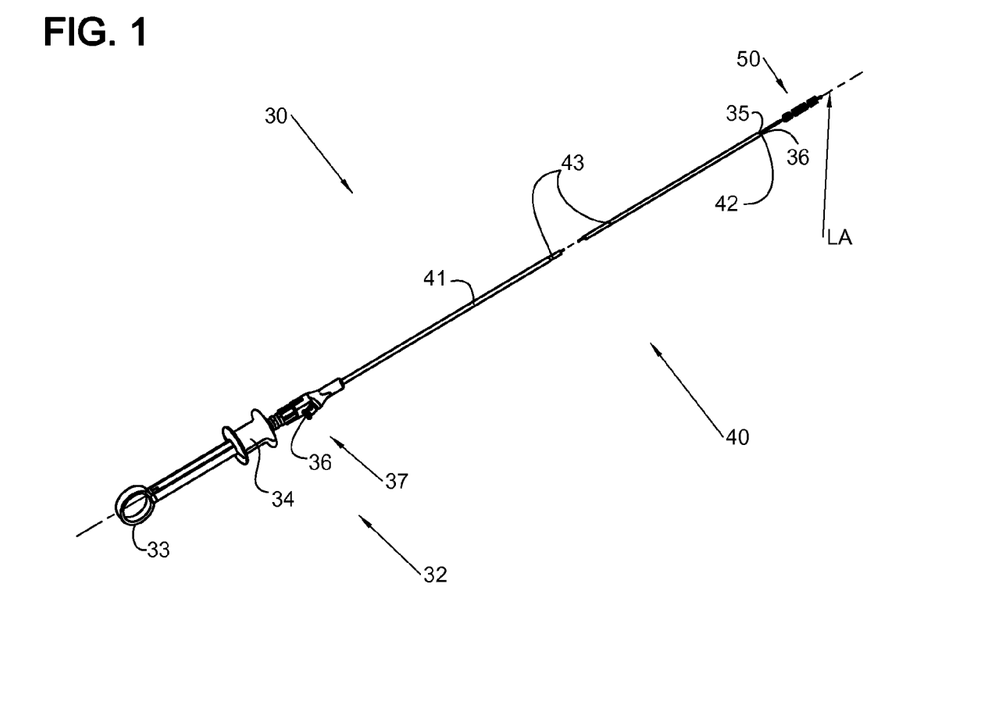
FIG. 1 is an is an isometric view of an improved cytology brush apparatus having a handle assembly, a flexible cannula, and a improved cytology brush shown in an extended position.
Figure 3:
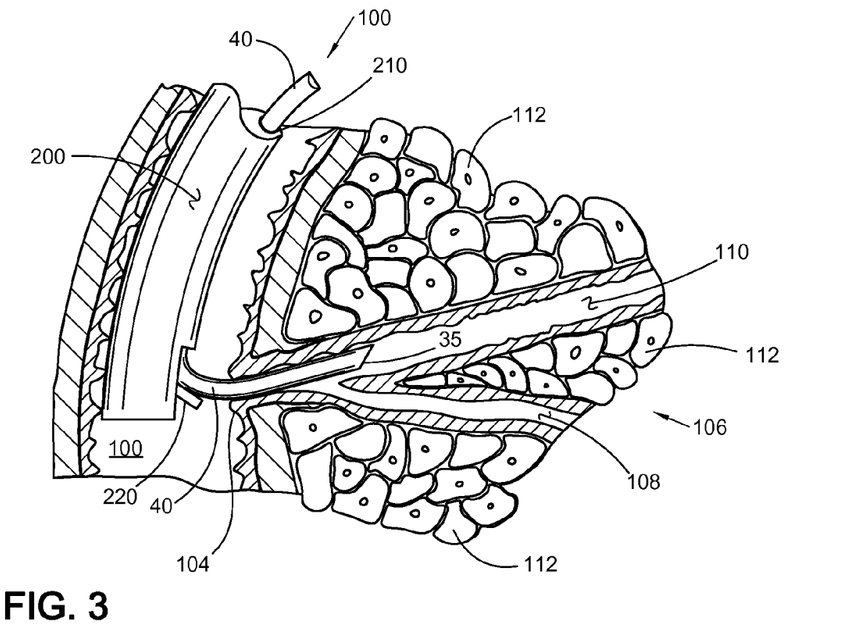
FIG. 3 is a side cross sectional view of the duodenum and biliary tract, an endoscope is shown positioned therein with a distal end of the improved cytology brush apparatus inserted into the biliary tract.

FIG. 1 is an isometric view of an improved cytology brush apparatus 30 that can be used to acquire, store, and remove cell samples from a human patient, and can be used to access tissue within a patient either with or without an endoscope 200 (FIG. 3). Improved cytology brush apparatus 30 can be suited for acquiring soft tissues such as mucosal and submucosal tissue from areas such as the upper and lower gastrointestinal tract. Improved cytology brush apparatus 30 has a proximally located handle assembly 32, a flexible cannula 40 extending distally therefrom, and an improved cytology brush 50 at a distal end. The cytology brush 50 is operatively configured to extend from and retract into the cannula 40 in response to operator manipulation of the handle assembly 32, and is shown in an extended position in FIG. 1. Cytology brush 50 is normally stored or retracted within the flexible cannula 40 to prevent contamination, and can extend from the cannula 40 in response to an operators actuation. In some surgeries, two brush extensions are used. The first extension is at the surgical site within the patient to acquire the tissue sample, and the second extension is done outside of the patient after the cells have been acquired to transfer the acquired tissue sample into a storage medium for cellular analysis. Flexible cannula 40 is configured to slidably fit within an access port (not shown) and into an operative channel 210 (see FIG. 3) of the endoscope 200 so that the improved cytology brush 50 can use the endoscope 20 to reach a surgical site within a patient.

Figure 2:
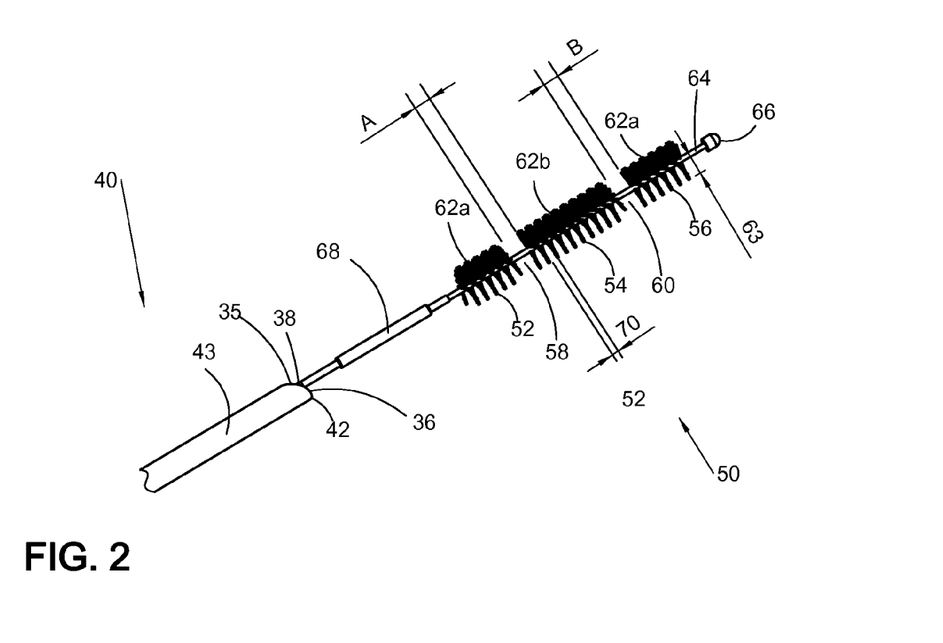
FIG. 2 is an enlarged isometric view of the improved cytology brush of FIG. 1.

Handle assembly 32 can comprise a first handle 33 and a second handle 34. Handle assembly 32 is operatively configured so that movement of one handle 33, 34 relative to the other handle 33, 34 results in extension and retraction of the improved cytology brush 50 from the flexible cannula 40. In the preferred apparatus shown in FIG. 1 but not limited thereto, the first handle 33 is configured to be held fixed in the operator's hand, such as on a finger or thumb, and the second handle 34 is configured to be movable relative thereto. Flexible cannula 40 can include an exterior sleeve such as an inner catheter 43 and a strain relief 41 around catheter 43. Cannula 40 will usually be sized to fit within an operative channel of a rigid or a flexible endoscope 200, and can have a proximal end of the flexible cannula 40 fixedly attached to the first handle 33. A longitudinal axis "LA" extends through both the improved cytology brush 50 and handle assembly 32, and defines a direction of motion for the brush 50 and one or more handles 33, 34. An open first passageway 35, with an inner surface 35a and a distal opening 35b, (see FIG. 7) may extend longitudinally through both the handle assembly 32 and the flexible cannula 40. This passageway 35 can extend from handle 32 to distal end 42. In the exemplary preferred embodiment shown in FIG. 1, a flexible wire or drive cable 38 (see FIG. 2) can movably extend through the first passageway 35 to interconnect the movable second handle 34 to the improved cytology brush 50 via a wire coupler 68 (FIG. 2). This interconnection can enable brush 50 to be withdrawn into and extended from the first passageway 35 in response to movement of the second handle 34 relative to the first handle 33.

At least one other open passageway can be optionally provided such as a second passageway 36 (see FIG. 7) extending at least in part longitudinally parallel to the first open passageway 35. As shown in the example of FIG. 1, the second passageway 36 can extend longitudinally from an access port 37 on the handle assembly 32 and can emerge at a distal end 42 of the cannula 40 parallel to the distal opening 35a of first passageway 35. Second passageway 36 can be provided as an access passage for additional surgical instruments such as but not limited to a guidewire. Passageway 36 can also be used to deliver fluids such as saline, drugs, tissue preparation solutions, contrasting agents and the like to the cell extraction site.

Modern cytology brush devices are frequently constructed from a brush comprising a continuous cylindrical brush of uniform stiffness bristles. The stiffness of the bristles must be stiff enough to abrade tissue from a surgical site, yet soft enough to fold up during insertion and withdrawal from the patient. Another consideration of the bristle stiffness/softness issue is that some skilled in the art believe that the softer bristles offer better acquisition and retention of the listened abraded cells. Stiffer brushes can be optimal for abrasion of cell samples, but can produce high frictional forces when extended from and withdrawn into the cytology brush devices. This can pose challenges with proper brush deployment, and with cell collection. Softer brushes have lower frictional forces during extension and retraction, and are believed to be better at collecting loose cells, but can have difficulty abrading cells from tissue. A brush with a single bristle stiffness can face challenges in being stiff enough to optimize tissue abrasion, while being soft enough to maximize tissue sample collection.

FIG. 2 is an enlarged isometric view of the exemplary preferred embodiment of the improved cytology brush 50. Improved cytology brush 50 provides improvements over prior art brushes, and can offer improved cell removal and extraction from a surgical extraction site. One exemplary embodiment is best shown in FIG. 2 where the improved cytology brush 50 comprises a proximal brush portion 52, a central brush portion 54, and a distal brush portion 56. As will be described in greater detail below, one or more of these multiple brush portions 52, 54, 56 can be optimized for abrasion, and the remaining brush portions can be optimized for tissue collection.

Each brush portion 52, 54, 56 can be cylindrical in shape and can comprise a plurality of bristles 62 that can extend radially from a flexible or rigid shaft 64 that connects to cable 38. As shown in FIG. 2, the radially extending bristles 62 can usually extend spirally around the shaft 64, and can be of a generally uniform length extending from shaft 64. Shaft 64 is usually substantially solid without an open through passageway within, and can comprise a single member shown in FIG. 2. A brush tip 66 can be provided at a distal end of cytology brush 50 to provide an atraumatic tissue contact surface, and the wire coupler 68 can be provided at a proximal end to couple cytology brush 50 to cable 38. Wire coupler 68 can be a crimp, a weld, an adhesive or any other attachment. A proximal gap 58 and a distal gap 60 may extend longitudinally to separate the brush portions 52, 54, 56 and to act as a tissue collector for improved tissue sample collection and retention. The tissue collection capabilities of the proximal and distal gaps 58, 60 and aspects thereof will be discussed in greater detail below. As shown, shaft 64 extends along a longitudinal length of the improved cytology brush 50 and bridges across longitudinal gaps 58, 60.

As shown in the present embodiment of FIG. 2, the three brush portions 52, 54, 56 can have a brush diameter larger than the cannula, and two or more brush portions can have the same diameter around the shaft 64. Brush portions 52, 54, 56 and can be constructed from filaments or bristles 62, which can have the same or different material properties. With the exemplary embodiment of FIG. 2, promising test result were obtained when the proximal and distal brush portions 52, 56 have stiff bristles 62a, and when the central portion 54 has soft bristles 62b. Testing showed the stiffer bristles 62a of the proximal and distal portions 52, 56 rub, abrade and loosen cells at the surgical site, and the softer bristles 62b of the central section 54 can acquire and shield the abraded cells within the bristles 62b and within the gaps 58, 60. Bristles 62 are configured to fold or bend when brush 50 is drawn into first passageway 35 and to expand when brush 50 moves out of the first passageway 35. This process will be described in detail below.

The bristles 62 of the preferred embodiment of the improved cytology brush 50 of FIG. 2 are usually formed from nylon, bristles 62a of the proximal and distal brush portions 52, 56 are 0.007 inches in diameter, and bristles 62b are 0.003 inches in diameter for the central portion 54. Brush portions 52, 54, 56 can be generally cylindrical, and can have a diameter between about 0.005 inches and about 1.500 inches. In the exemplary embodiment of FIG. 2, the outer diameters of the brush portions 52, 54, 56 are about 0.188 inches. For the about 0.188 inch diameter, exemplary results were obtained with bristles 62a, 62b that had a bristle length 63 of about 0.083 inches extending from shaft 64. Gaps 58, 60 are located between the three brush portions 52, 54, 56, and can be between about 0.0005 inches and about 6 inches. Exemplary gaps are shown in FIG. 2 and can have gap lengths "A" and "B" as shown which can be about 0.083 inches along the longitudinal axis. The exemplary gap of 0.083 was found to produce increased tissue collection when the diameter of the brush portion 52, 54, 56 is about 0.188 inches. This relationship between gap and brush diameter will be described in greater detail below. A bristle gap 70 exists between adjacent spiral portions of the bristles for the reception of tissue samples or cells therebetween.

An additional advantage of the gaps 58, 60 found within the present apparatus is a measurable reduction in brush extension and retraction force. The drag force occurs between the cytology brush 50 and the cannula 40 and is encountered whenever the improved cytology brush 50 is being extended from or withdrawn into the first passageway 35. During extension, the force of the folded bristles 62 pushing against inner surface 35a of first passageway 35 creates the frictional drag force encountered. During retraction, the folded bristles 62 create a frictional drag force by pushing against inner surface 35a of the first passageway 35 and an additional folding drag force comes from the bending or folding of the bristles 62 as they are drawn into the first passageway 35. Thus, during retraction, the drag force is a combination of the frictional drag force and the force needed to bend or fold the bristles 62. A reduction in force is accomplished by the improved cytology brush 50 in two ways. First, the softer bristles 62b require less energy to bend than the stiffer bristles 62a and a reduction in energy input is obtained by merely providing a brush portion with softer bristles 62b. Second, the soft bristles 62b reduce the force pressing outward against the first passageway 35 which reduces the overall frictional drag force. Thus, providing the improved cytology brush 50 with a portion of soft bristles 62b reduces the frictional drag force and the bristle bending force.

Second, each of the gaps 58, 60 reduce bristle drag and bending forces by removing some of the bristles 62 from the brush 50. The gap portions 58, 60 have no bristles 62, and thus cannot produce a bristle folding force or a bristle drag force with the first passageway 35. Reducing brush extension and retraction forces can be of great benefit in certain surgeries where the cannula must undergo a sharp bend to access hard-to-reach surgical sites like the biliary tract. Thus, the design of the improved cytology brush 50 can usually improve deployment and retraction of the brush 50 in these conditions.

FIGS. 3-6 show a cross sectional view of a portion of a duodenum 100 and biliary tract of a patient. The FIGS. 3-6 provide an exemplary illustration of a series of steps where the improved cytology brush apparatus 30 is used to acquire a tissue sample from a cystic duct. In FIG. 3, an endoscope 200 has been inserted into the patient's mouth, has passed through a stomach of the patient (not shown), through the pyloric junction (not shown) and is positioned within the duodenum 100 adjacent to a duodenal papilla 104 that marks the entrance to a biliary tract 106 of the patient. The flexible cannula 40 of the improved cytology brush apparatus 30 has been inserted into the access port of the endoscope 200 and has emerged from a distal end of the operative channel 210. An elevator or flapper 220 of the endoscope 200 has been actuated to sharply bend the emerging distal end 42 of the cannula 40 so that it can be inserted into the duodenal papilla 104, and into the bilary tract 106. In this view, the distal end 42 of the cannula 40 has bypassed the pancreatic duct 108 and is entering the cystic duct 110 adjacent to a pancreas 112. The improved cytology brush 50 is not seen in this view because the brush 50 is withdrawn into the first passageway 35 of the cannula 40 to protect against brush contamination caused by inadvertent contact with tissue or a contaminated endoscope 200.

Figure 4:
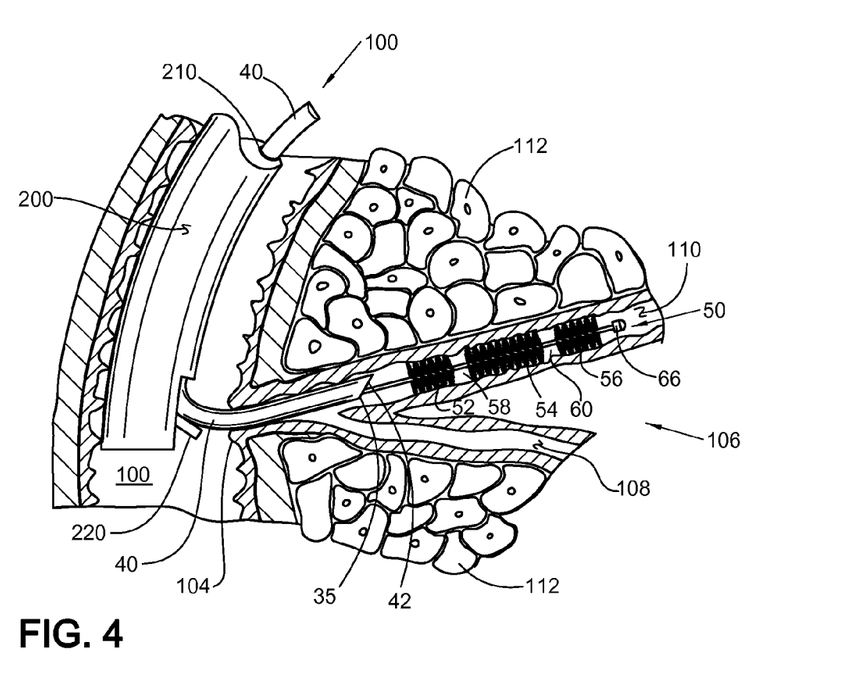
FIG. 4 is the side cross sectional view of FIG. 3 where an improved cytology brush is extended into a cystic duct of the biliary tract to acquire a tissue sample therefrom.

FIG. 4 shows the improved an improved cytology brush 50 extended from the cannula 40 and making contact with tissue at the desired spot within the cystic duct 110.

Figure 5:
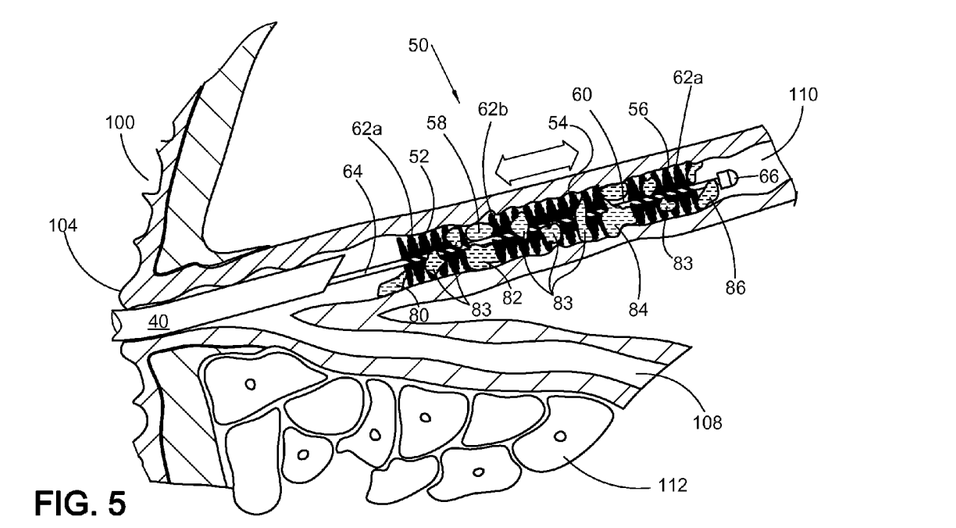
FIG. 5 is an enlarged side cross sectional view of FIG. 4 wherein the improved cytology brush is shown being moved proximally and distally to acquire tissue samples from the cystic duct.

In FIG. 5, the brush 50 is being rubbed back and forth in the longitudinal direction (see arrows) to brush or scrape tissue samples 80, 82, 83, 84, 86 from the inside of the cystic duct 110 with the stiff proximal and distal brush portions 52, 56 respectively, and with the soft central brush portion 54. Tissue samples 83 are collected within brush 50 between bristles 62, and within gaps 58, 60. The back and forth rubbing action can be accomplished by having the operator of the improved cytology brush apparatus 30 manipulate the handles 33, 34 of the handle assembly 32 to move the brush 50 back and forth, or by having the operator push and pull the cannula in and out of the operative channel 210 of the endoscope 200. In this view, the primary tissue abrasion is accomplished by stiffer proximal and distal portions 52, 56 of the improved cytology brush 50 with lesser tissue abrasion from the softer central portion 54. Tissue samples 82, 83, and 84 are being acquired within the softer central portion 54 and within gaps 58, 60. Tissue samples 83 are also collected between bristles 62a, in the stiff brush portions 52, 56, and in between bristles 62b of the soft brush portion 54 respectively. The tissue samples 80, 82, 84, 86 can accumulate in front of and behind the stiff brush portions 52, 56. As shown, the rubbing action has placed a large number of cells within the gaps 58 and 60 located between the brush portions 52, 54, 56. The unexpected ability of the gaps 58, 60 to act as a collector to increase the size of the acquired tissue samples will be discussed in detail below. In this view, some of the tissue of the pancreas has been removed from the tissue model of FIG. 4 to provide element number clarity.

Figure 6:
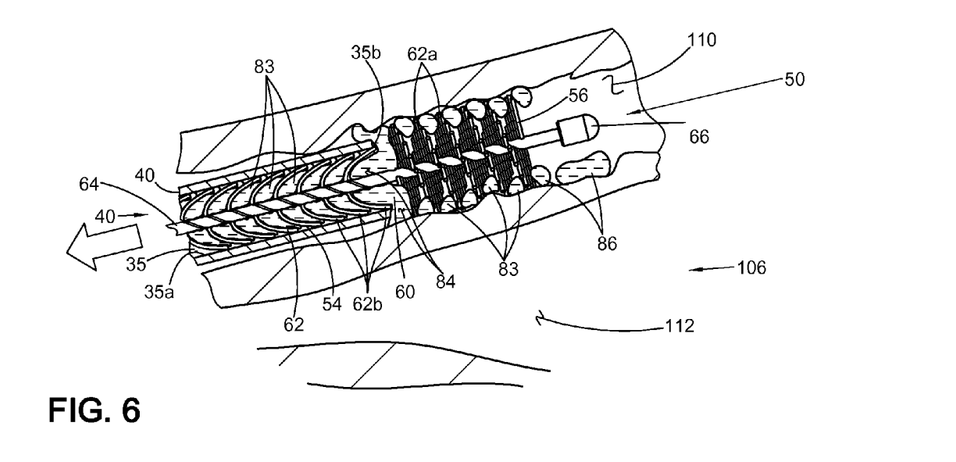
FIG. 6 is an enlarged partial top cross sectional view of FIG. 5 wherein the improved cytology brush is shown being retracted into a partially sectioned flexible cannula with a distal brush portion fully extended and a central brush portion being folded over a distal gap between the proximal and distal portions to shield tissue samples within the distal gap.

In FIG. 6, the operator has rubbed the cytology brush 50 across the surgical site and has acquired a sufficient amount of tissue 84, 85 within the brush 50 for analysis. In this view, the improved brush 50 is being withdrawn into the open first passageway 35 of flexible cannula 40 by moving brush 50 to the left as indicated by an arrow. The improved cytology brush 50 is shown partially withdrawn into the first passageway 35 of the cannula 40 such that only the distal portion 56 is fully extended outside of the cannula 40. The bristles 62b of the central brush portion 54 are folded over in the first open passageway 35 with just a distal tip of the distalmost folded bristles 62b extending from the distal opening 35b of open passageway 35. The extended tips of bristles 62 extending from the distal opening 35b of open passageway 35 fold across gap 60 to collect and protect an enlarged portion of tissue samples 82, 84 as follows.

The withdrawing action shown in FIG. 6 has engaged the sides of bristles 62a with first the distal opening 35b and second the distal inner surface 35a of the first open passageway 35 to fold bristles 62a over. As the bristles 62a fold over, the folding contact with the cannula 40 can squeegee or wipe some of the tissue samples 83 from the folding bristles 62b of the central brush portion 54. The squeegeed tissue 83 can accumulate at the distal opening 35b of the first open passageway 35 and the accumulation can increase the tissue sample size retrieved for analysis by being packed into the gaps 58, 60 as the brush 50 withdraws. Tissue samples 84 that are collected and stored within the gap 60, can be advantageously shielded from the wiping contact of the distal opening 35b and inner surface 35a by the folded bristles 62b of the central brush portion 54. Thus, in FIG. 6, folded bristles 62b fold across gap 60 and shield the tissue samples 84 trapped thereebeneath. While not shown in this view, the same process enables a similar large portion of gap tissue samples 85 to be collected and protected within proximal gap 58 (see FIG. 5) by the folding of the bristles 62a of the proximal brush portion 52 (see FIG. 5). Thus, gaps 58, 60 can advantageously collect and store large quantities of gap tissue portions 85 within, and adjacent bristles 62a, 62b respectively, fold across gaps 58, 60 to protect and shield gap tissue samples 85 found within from being wiped off by cannula 40. Note that the gaps 58, 60 lack bristles 62, 62a, 62b, and the missing bristle volumes can provide extra tissue storage volume within gaps 58, 60. Additionally, in embodiments where the bristles can fit within the cannula 40 without folding, the gaps 58, 60 can increase sample size by providing additional sample storage space over conventional brushes without the gaps 58, 60.

One additional advantage of having stiff bristles 62b at opposing ends of the brush 50 is the tendency of the stiffer bristles 62 to lift the brush 50 away from an inner surface of a contact surface such as the common bile duct 110 (FIG. 5) so that maximum quantities of cells can be accumulated between the proximal and distal brush portions 52, 56, and in tissue collectors or gaps 58, 60. When the brush 50 is drawn into the first passageway 35 of the cannula 40 as shown in FIG. 6, the stiff bristles 62 center the brush 50 within the first passageway 35 and keep the shaft 62 lifted away from the inner surface 35a thereof. The centering action ensures that maximum quantities of tissue samples are accumulated and maintained between brush portions 52, 56, and ensure that tissue collected within tissue collectors or gaps 58, 60 remain a maximum possible distance away from the wiping action of distal opening 35b to thereby maximize tissue sample collection.

Once the improved cytology brush 50 is fully withdrawn into the first passageway 35 of the cannula 40 by manipulation of the handle 32, the brush 50 is protected from contamination and the cell samples are ready to be removed from the patient. The cell sample is removed by withdrawing the cannula 40 from the operative channel 210 and access port of the endoscope 200 (not shown). Once the cell samples trapped within the improved cytology brush 50 are outside of the patient, the brush 50 can be extended from the open passageway 35 of cannula 40 and the acquired cell samples can be rinsed and extracted from the improved cytology brush 50 by the clinicians preferred method. One exemplary method of cell extraction is dipping and agitating the brush 50 in a bath of transport or preservation media such as CytoLyt® made by Cytyc Corporation, Boxborough, Mass.

It is of note that within FIG. 6, the distal gap 60 of the improved cytology brush 50 has acquired a large sample of tissue therein, and the bristles 62b of the central brush portion 54 have folded over to protect and shield the tissue sample beneath the bristles 62b. The gap 80 is operably configured such that when the bristles 62b are folded over in the open passageway 35 of flexible cannula 40, a longitudinal length "B" (see FIG. 2) of the gap 80 is usually about the same length as a folded over bristle 62b. Likewise, a length "A" of gap 58 between the proximal and central brush portions 54, 56 follows this same ratio of gap and length of folded over bristles 62a. Thus, for the exemplary preferred embodiment of the improved cytology brush 50 as shown in FIGS. 1-6 but not limited thereto, the brush 50 can have an outer diameter of about 0.188 inches, the bristles 62a, 62b can have a bristle length of about 0.083 inches as measured from shaft 64, and gaps 58, 60 located between the three brush portions 52, 54, 56, can be about 0.083 inches as measured longitudinally along shaft 64. Note that for this example, the gaps 58 and 60 are about the same length (0.083 inches) as the bristle length (0.083 inches), but other gaps and bristle lengths are possible and the present apparatus is are not intend to be limited thereto.

Figure 7:
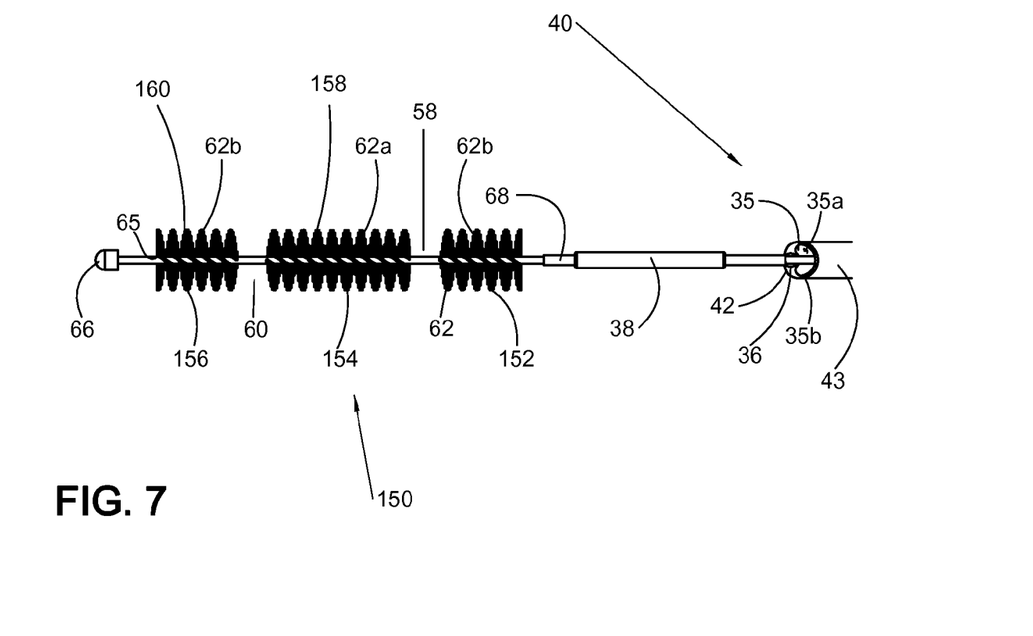
FIG. 7 is a side view of an alternate embodiment of the improved biopsy brush wherein the brush comprises a soft proximal brush portion separated from a soft a distal brush portion by a stiff central portion and with gaps placed therebetween.

FIG. 7 illustrates another exemplary embodiment of the present apparatus. In this embodiment, a brush 150 has a proximal brush portion 152, a distal brush portion 156 and a central brush portion 154. Gaps 158, 160 separate and isolate each brush portion 152, 154, 156 from adjacent brush portions. This embodiment of FIG. 7 differs from the embodiment of FIG. 2 in that the material properties of the bristles 62 such as hardness and softness is different. That is, the proximal and distal brush portions 152, 156 of FIG. 7 comprise soft bristles 62b, and the central brush portion 154 comprises stiff bristles 62a. FIG. 7

It is also understood that the present apparatus is not limited to the three exemplary brush portions 52, 54, 56, shown in FIGS. 1-7, but can comprise any number of brush portions greater than one. An exemplary embodiment of an alternate cytology brush 250 that has two brush portions separated by a gap 258 is shown in FIG. 8.

Figure 8:
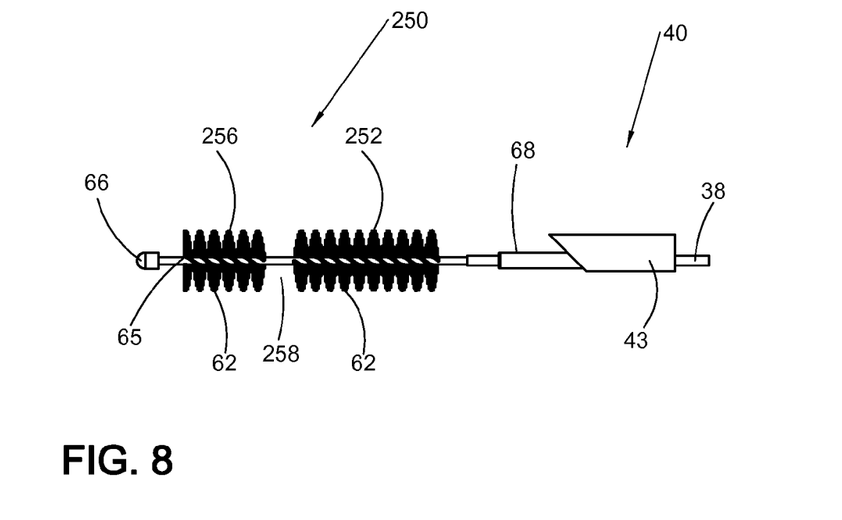
FIG. 8 is a side view of an alternate embodiment of the improved biopsy brush wherein the brush comprises a proximal and a distal brush portion with a gap therebetween.

In FIG. 8, the cytology brush 250 comprises a proximal brush portion 252, a distal brush portion 256, and has a single tissue collector or gap 258 therebetween. As shown, each brush portion 252, 256 of the present apparatus may have bristles 62 that have the same material properties usually hardness and softness. Alternately, in another embodiment of the present apparatus, the distal brush portion 256 has hard bristles 62a, and the proximal brush portion 252 has soft bristles 62b. In yet another embodiment of the present apparatus, the distal brush portion 256 has soft bristles 62b, and the proximal brush portion 252 has hard bristles 62a. Thus, for any cytology brush 50, 250 having at least two brush portions with a tissue acquiring gap between adjacent portions, any combinations of material properties can be used and fall within the spirit of the apparatus.

Additionally, each cytology brush of the embodiments of the present apparatus can have a tissue collector, usually a gap 58, 60, 158, 160, 258, 260 found between bristle portions of embodiments of the improved brush 50. The number of tissue collectors or gaps such as gaps 58, 60, 158, 160, 258, 260 for the improved cytology brush 50 of the present apparatus is at least one, but can be greater. A longitudinal length of the gap such as "A" and "B" of FIG. 2 can be the same or different on an improved cytology brush 250 and can range from wide to narrow. Brush portions in embodiments described above usually have different material properties such as the exemplary brush portions 52, 54, 56. In other embodiments of the present apparatus, a longitudinal length of the tissue collector, usually gaps 58, 60, 158, 160, 258, 260 can be minimized to bring together one or more of the brush portions such as portions 52, 54, 56.

Figure 9:
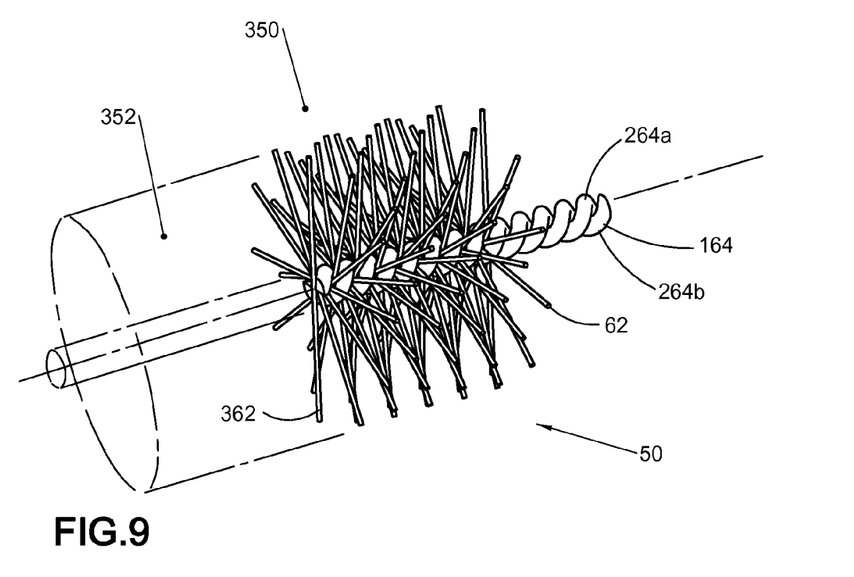
FIG. 9 is an isometric view of a partially sectioned view of an alternate twisted wire brush shaft embodiment.
Figure 10:
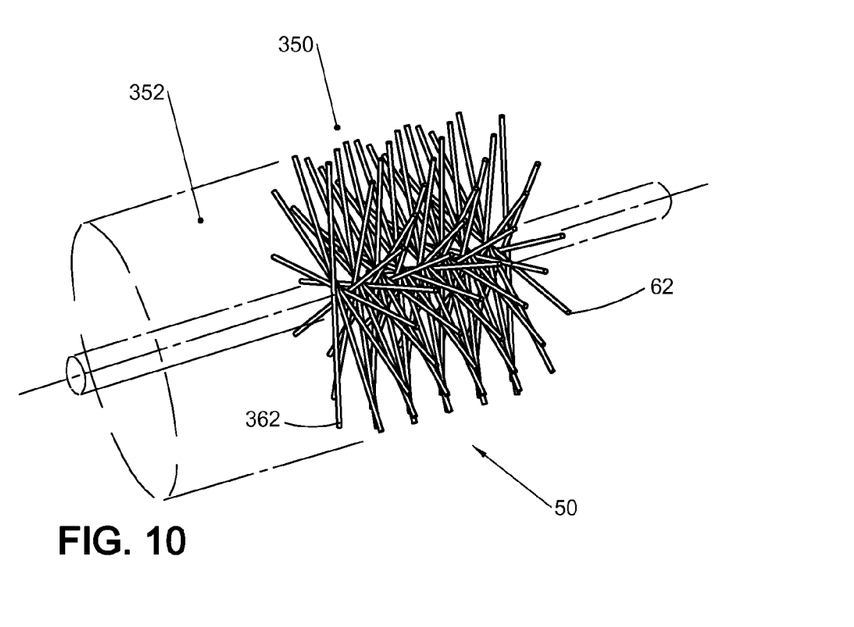
FIG. 10 is the isometric view of FIG. 9 wherein the twisted wire shaft is removed to show how bristles are oriented.

FIGS. 9 and 10 illustrate a partial section view of exemplary embodiments of the brush 50. The partial section views are provided to illustrate the method of construction of this embodiment. In this embodiment of the present apparatus, the improved cytology brush 50 is shown as a sectioned brush portion 350 with sectioned portions 352 of the sectioned brush 350 shown as dashes lines for clarity. Sectioned brush portion 350 can comprise a plurality of bristles 62 that are captured by twisting between a pair of parallel wire legs 264a, 264b together to form a shaft 164. Prior to the twisting operation, the bristles 62 can be oriented and held in parallel between legs 264a, 264b, and can be touching. In FIGS. 9 and 10, the bristles 62 were both parallel and touching prior to twisting, and reoriented after twisting to the positions shown. In FIG. 9, brush portion 350 is shown sectioned with the removed portion in outline. An end bristle 362 is clearly visible captured between the legs 264a, 264b at the section cut. The bristles 62, such as end bristle 362, are usually generally elongated members, and can pass through the longitudinal axis of brush 50. As shown, bristles 62, 362 can extend equidistant from the shaft 162, and in embodiments, bristles 62, 362 can be arcuate along at least a portion of the generally elongated members. Wire legs 264a, 264b can be formed from at least one piece of wire.

FIG. 10 is the view of FIG. 9 with the shaft 164 shown in phantom view to better show bristles 62, 362 and their orientation. As shown, brush portion 350 is a plurality of single bristles 62, 362 that are touching adjacent bristles along the longitudinal axis "LA" to form a helix of bristles 62, 362. Each bristle 62, such as bristle 362, is a single bristle that can extend on either side of shaft 164.

Figure 11:
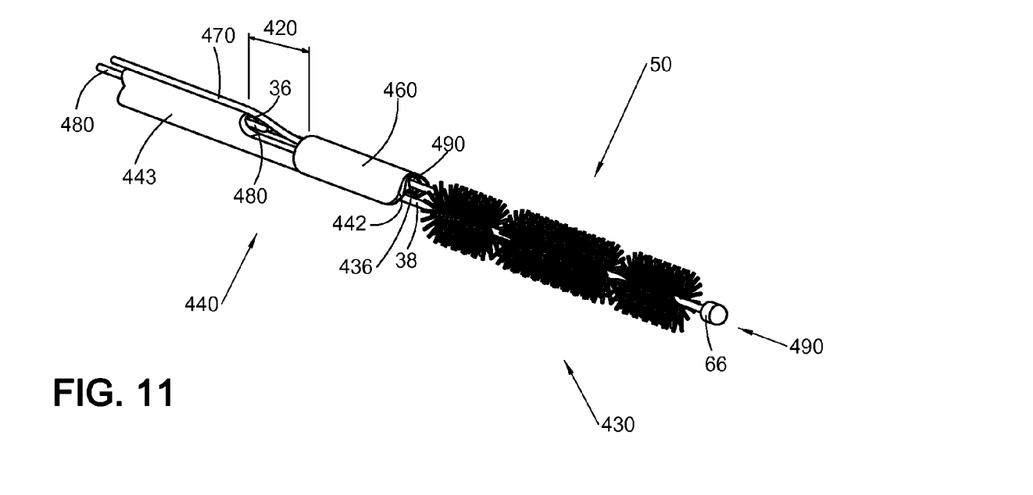
FIG. 11 is an isometric view of a proximal end of an improved cytology brush apparatus configured to be used with and guided by a short guidewire or a long guidewire.
Figure 12:
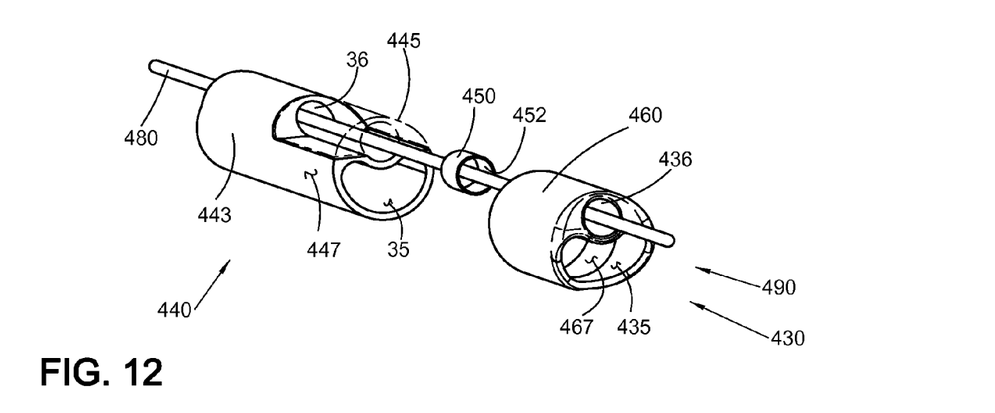
FIG. 12 is an isometric exploded view of FIG. 11 showing the elements of the guidewire configuration.
Figure 13:
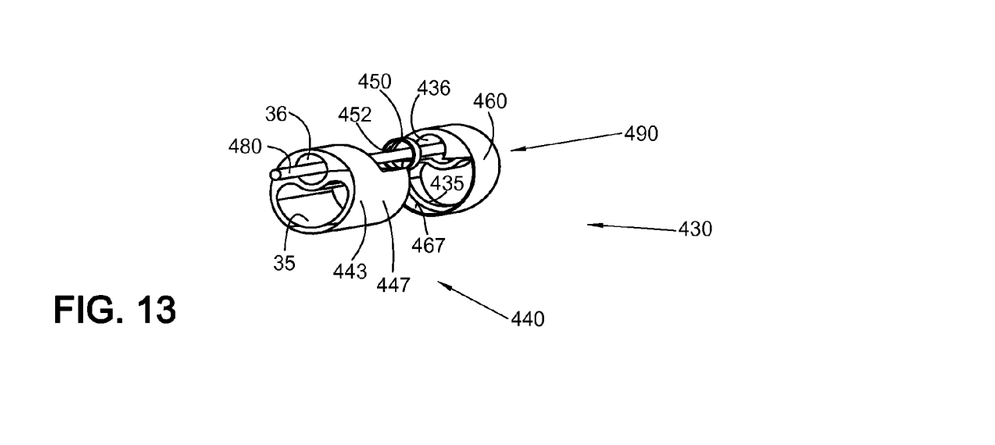
FIG. 13 is a rear isometric exploded view of a FIG. 11 showing the elements of the guidewire configuration spaced apart.

FIGS. 11-13 show an alternate embodiment of the improved cytology brush apparatus 30 wherein the flexible cannula 40 is replaced with an improved flexible cannula 440 configured to work with both a long guidewire, and with a short guidewire.

Guidewires are frequently used in endoscopic surgery as a means of guiding one or more surgical devices, such as improved cytology brush 50, to a surgical site such as a patient's duct, organ or vessel. The short and long guidewires can be placed through an operative channel of the endoscope (not shown), and may be guided into position via imaging technology such as ultrasound or X-rays, or by direct visualization. Once the guidewire is in position, surgical devices can be placed onto the guidewire outside of the patient, and slid or guided to the surgical site via the guidewire first through the endoscope, and then through the patient. After surgeries, guidewires are removed. Various methods of using guidewires exist, and are a matter of surgical preference.

FIG. 11 shows a distal end of the improved flexible cannula 440 that can be attached to the handle assembly 32 (see FIG. 1) to create an alternate improved cytology brush apparatus 430. Cytology brush apparatus 430 is adapted for use with a short guidewire 470, or with a long guidewire 480. The improved cytology brush apparatus 430 comprises a proximal flexible cannula 443 with a distally located attached catheter tip 460. Improved flexible cannula 440 has a distal end 442 located at a distal end of attached catheter tip 460. The alternate cannula 440 can be molded in the configuration shown in FIGS. 12-13, or can be fabricated from the previously described cannula 40 by removal of at least a distally located cut portion 445 shown in outline in FIG. 12. Removal of the cut portion 445 leaves a distal extension 447 that can engage with the catheter tip 460. As shown in FIGS. 11-13, distal extension 447 can engage within a receptacle 467 that extends at least partially into a proximal end of attached catheter tip 460. This engagement can be a locking engagement such as, but not limited to a press fit, a snap fit, a glue joint, or an overmolding of attached catheter tip 460 onto distal extension 447. In an alternate embodiment, the proximal flexible cannula 443 can be first assembled with catheter tip 460, and then a portion of the cannula 443 can be cut away.

As best shown in FIGS. 12 and 13, alternate cannula 440 includes the circular shaped second passageway 36 and the "smile shaped" first passageway 35. Second passageway 36 extends longitudinally through cannula 440 to openly connect with the second passageway 36 in the handle assembly 32, and first passageway 35 is configured to receive the drive cable 38 and brush 50 within.

The attached catheter tip 460 can have a "smile shaped" first tip passageway 435 and a "circular shaped" second tip passageway 436 extending therethrough. When catheter tip 460 is attached to the flexible cannula 443, the first and second passageways 435, 436 within the tip 460 align with the first and second passageways 35, 36 respectively, of the flexible cannula 443. First passageways 35, 435 can be identical in size and shape to provide unimpeded passage of the drive cable 38 and brush 50 as they are extended from and retracted into alternate cannula 440 during the acquisition of samples. Second passageways 36, 436 can also be of similar size and shape for unimpeded passage of guidewires or other instruments within. A gap 420 extends between first passageways 35, 435 for the passage of a guidewire such as short guidewire 470 or long guidewire 480 within. Note that guidewires 470, 480 use gap 420 differently.

The circular first passageway 436 can be configured to receive and restrain a marker tube 450 therein. Marker tube 450 can be a hollow cylinder configured to include materials to improve visibility of the distal tip 442 when using ultrasound and or radiological viewing. As such, marker tube 450 can include barium salts or metals to enhance visualization, and can be attached by becoming glued, molded, snapped into place or press fit. Marker tube 450 can have an inner bore 452 that is configured to align with circular first passageways 36 and 436. In an embodiment, passageways 36, 436, and bore 452 can be the same diameter which can slightly increase an outer diameter of the marker tube 450. For this embodiment, at least a portion of the first tip passageway 436 can be enlarged to accommodate the slightly larger outer diameter of the marker tube 450. In yet another embodiment, marker tube 450 can extend proximally to distally along the entire length of first tip passageway 436 in attached catheter tip 460. The combination of bore 452 and first tip passageway 436 can form a uniform diameter open passageway such as a guide passage 490 that extends through the attached catheter tip 442. Guide passage 490 is provided for the unimpeded passage of surgical devices like short guidewire 470 and long guidewire 480 therethrough.

As shown in FIG. 11, passageways 36, 436 and bore 452 are aligned. A short guidewire 470 is shown inserted through guide passage 490 of the tip 460 to exit from the gap 420. As the tip 460 is guided along the guidewire to the surgical site, the short guidewire 470 lies parallel to the flexible cannula 443 as shown. In the view of FIG. 12, a distal end of the short guidewire 470 protrudes from the tip 460 and into the brush 50. This positioning of guidewire 470 and tip 460 may occur when the distal tip 442 of the improved cytology brush apparatus 430 has been guided to the surgical site to collect tissue specimens with brush 50. In FIG. 11, the brush 50 and the drive cable 38 are shown extending from the first passageways 35, 435 for the collection of tissue.

The improved cytology brush apparatus 430 is also configured to work with the long guidewire 480. In FIGS. 11 and 12, partial exploded views are provided showing the flexible cannula 443, marker tube 450, and catheter tip 460 exploded longitudinally along the long guidewire 480. This provides an exemplary illustrational view of how the proximal flexible cannula 443 and catheter tip 460 of the improved cytology brush apparatus 430 are configured to receive and to be guided by the long guidewire 480 during operation. For illustrational purposes, guidewire 480 is also shown in FIG. 11 extending slightly from second passageway 36 and in this position, guidewire 480 will extend along second passageway to emerge from the handle assembly 32. Whereas the above description of improved flexible cannula 440 is described for use with a cytology brush 50, the improved flexible cannula 440 is not limited to use thereto.

In alternate embodiments of the present apparatus, the bristles 62 can be attached to the shaft 64 in the manner found in plastic toothbrushes where one or more bristles 62 can extend from an opening 65 in the shaft 364 (see FIG. 7). At least a portion of bristles 62 can reside within at shaft 364, and bristles 62 can be secured within the at least one opening 65 by adhesives, press fit of bristles in the opening 65, over molding and the like. With this method of bristle 62 attachment, different arrangements of bristles 62 or patterns of bristles 62 are available for the present apparatus such as but not limited to circular rings of bristles 62 radiating from the shafts 64, 364 with longitudinal tissue collecting gaps therebetween, multiple portions of bristles of different properties and the like. In embodiments, shafts 64, 364 can be metal or plastic.

In yet another alternate embodiment of the present apparatus (not shown), the bristles 62 attached to the substantially solid shaft can form one or more circular disks of bristles 62 protruding from shafts 64, 164, 364. Multiple circular disks of bristles 62 can be spaced longitudinally along shafts 64, 164, 364 and can provide exemplary tissue traps or tissue storage areas between adjacent circular disks of bristles 62. Circular disks of bristles 62 can extend perpendicularly from shafts 64, 164, 364.

The above described material properties for the bristles 62 such as bristles 62a, 62b of the present apparatus are meant to be exemplary, and the characteristics listed above are not meant to limit in any way the material properties that can exist for the bristles 62 of any embodiment of the improved cytology brush apparatus 30. The material characteristics of the bristles 62 within each brush portion can be the same or can be different from adjacent brush portions such as the exemplary brush portions 52, 54, 56 shown in FIG. 2. Changes in the material properties of the bristles 62 of the present apparatus can result from material choice, size, shape, processing, surface finish, soft or stiff bristles, lubricity, hardness, roughness, bifurcation, material durometer, inherent surface grip such as tackiness of the material used, and or any other characteristics that one skilled in the art can use to alter the material characteristics of the bristles 62.

Acceptable exemplary embodiments of materials for use as bristles 62 of the present apparatus can include natural or biological materials, plastics, metals, or combinations thereof. Acceptable exemplary plastics can include, but are not limited to the previously mentioned nylon as well as, for example, polyethylene, polypropylene, urethanes, TPES, products containing PTFE (Teflon®), as well as fibers such as cotton, Rayon, Dacron and any other natural or artificial fiber. Acceptable metals can include but are not limited to stainless steel, titanium, nitinol, and nickel alloys. Bristles 62 of the present apparatus can be round, oval, triangular, square, rectangular, hexagonal, octagonal, or any other cross sectional shape, and the cross section can vary along a length of the filament. Bristles 62 extending from shaft 64 can be, in embodiments, straight, arcuate, folded, looped, bent, wavy or any other shape. Bristles 62 can be homogeneous or contain open or closed cell voids, and bristles 62 can range in diameter from about 0.0005 inches to about 0.050 inches across a widest portion of a bristle 62 cross section (not shown). Bristles 62 of the present apparatus can have surface finishes that are, for example, smooth, rough or notched to enhance tissue abrasion or tissue collection characteristics. Alternately, in yet another embodiment of the present invention but not limited thereto, one or more of the bristles 62 can be coated with a sticky coating to enhance cell collection such as but not limited to an elastomeric coating.

The exemplary bristles 62 shown in FIG. 2 can be equally spaced from adjacent bristles 62 by a bristle gap 70. This equal spacing is exemplary, and the bristle spacing 70 can be the same or different for each brush portions 52, 54, 56. If twisted wires (FIG. 9) are used to form shaft 164 and to constrain the bristles 62 therebetween, a diameter or width of the twisted wire legs 264a, 264b can be used to set the bristle spacing. Bristle spacing 70 can vary from between about 0.0005 inches to about 1 inch along the longitudinal axis, and can be in an exemplary embodiment about 0.045 inches from bristle center to bristle center.

With respect to a material characteristic that was described in the examples above as soft and stiff bristles, the stiff bristles 62a are not as easily bent as the soft bristles 62b, and have reduced deflection from a same applied load when compared to a soft bristle 62b. The stiffness or softness of a bristle 62 can be measured by a force deflection test where a force is applied perpendicular to a free end of the bristle 62, and the stiffness or softness of a bristle 62 can be measured as a unit of deflection for an amount of applied force. For the exemplary embodiment of the present apparatus of FIG. 2, all bristles 62 are made from nylon, have the same length, with the stiff bristles 62a measuring 0.007 inches in diameter and the soft bristles 62b measuring 0.003 inches in diameter. Softer bristles 62a or brushes can exhibit between about 1.1 and about 300 times more deflection than a stiff brush for a given force applied with the force deflection test, and for the exemplary embodiment shown, the softer 0.003 inch diameter nylon bristles 62b may deflect about 30 times more than the stiffer 0.007 inch diameter nylon bristles 62a.

In other exemplary embodiments of the present invention, the free end of the bristle 62 can be cut or modified to modify and or improve tissue collection. Exemplary cuts on the end of the bristle 62 can include but are not limited to a straight cut perpendicular to an elongate axis of the bristle 62, an angle cut to the elongate axis, a concave cut at the free end of the bristle 62, and a convex cut at the free end of the bristle 62. Partial cuts or notches can also be made along the bristle 62 to enhance tissue sample collection.

As shown in all FIGS, each of the brush portions 52, 54, 56 are cylindrical in shape. However, in alternate embodiments, one or more of the brush portions 52, 54, 56 can have alternate cross sectional shapes around the shaft 64 such as but not limited to: a triangle, a square, a rectangle, a hexagon and the like.

Additionally, other alternate embodiments in the spirit of the present apparatus can comprise brush with bristles 62 having a first long length from the shaft along brush portions, and having a second short length of bristles 62 between long length bristles 62 to create one or more tissue collectors or gaps between proximal and distal brush portions (not shown). These short bristle 62 gaps can usually be created by trimming the bristles 60 shorter, and can extend longitudinally along the brush portions as longitudinal troughs, or as helical spirals around the brush (not shown). That is, the improved cytology brush of the present invention can be formed as a continuous brush with the gaps 58, 60 cut or trimmed into place to better define the brush portions such as brush portions 52, 54, 56. With this trimmed gap embodiment, stubs of the bristles 62 can remain secured in the shaft 64 in the areas of the gap.

Each of the brush portions 52, 54, 56 can be made from bristles 62 having the same material properties as adjacent brush portions such as for example brush portions 52, 54, and 56, or from bristles 62 having different material properties from adjacent brush portions (52, 54, and 56). In one exemplary embodiment (not shown) to illustrate this ability but not limited thereto, the proximal portion 52 can have round stainless steel bristles 62 that have a 0.002 inch cross sectional diameter, a central portion 54 that can have 0.007 inch diameter bristles 62 made from polyethylene with open cell voids therein, and a distal portion 56 that can have nylon filaments 62 that are rectangular in cross section and measure 0.009 inches across the flats. Thus, alternate embodiments of the present apparatus can have any combinations of the material properties or geometries described above.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present apparatus has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, wire coupler 68 can be configured to be frangible so that the improved cytology brush 50 can be broken off to extract cell samples therefrom.

And, whereas bristles 62 are described above, other alternate embodiments of the present apparatus can use alternate materials in place of the bristles 62 such as hard and soft foam portions or other working equivalents thereof.

And in other embodiments, brush portions of the brush 50 can be cylindrical, but not limited thereto. For example, an improved cytology brush 50 of the present apparatus can comprise a number of spherical brush portions separated by gaps (not shown).

And for any of the above embodiments of the present invention, the improved cytology brush 50 can include a hollow shaft 462 (not shown), with a tissue collector between adjacent brush portions.

What is claimed is:

1. An apparatus for the collection and retention of tissue samples from within a patient, said apparatus comprising:
    a handle;
    a flexible cannula extending distally from the handle with a first inner lumen therein extending from the handle to a distal end of the cannula, the first inner lumen having an inner surface and a distal lumen opening at a distal end of the cannula; and
    a brush for collecting tissue samples, the brush movable in and out of the distal lumen opening in response to actuation of the handle, the brush comprising:
        i) a shaft extending from the inner lumen to define a longitudinal axis extending through the cannula to the handle,
        ii) a proximal portion of bristles extending cylindrically from the shaft, iii) a distal portion of bristles extending cylindrically from the shaft,
iv) a center portion of bristles extending cylindrically from the shaft, and disposed between the proximal portion of bristles and the distal portion of bristles, and
v) at least one tissue collector located between the proximal portion of bristles and the distal portion of bristles, the tissue collector configured to collect tissue samples within, and to retain the tissue samples as the brush is moved into the distal lumen opening of the cannula;
wherein the proximal portion and distal portion of bristles are stiff bristles for abrading tissue samples from the surgical site, and the center portion of bristles are soft bristles for collecting tissue samples abraded from the surgical site;
further wherein the center portion of bristles has a length along the longitudinal axis longer than either a length of the proximal portion of bristles or a length of the distal portion of bristles along the longitudinal axis.

2. The apparatus of claim 1 wherein the at least one tissue collector is a longitudinal gap between the proximal portion of bristles and the distal portion of bristles.

3. The apparatus of claim 1 wherein at least a portion of the bristles of the proximal portion of bristles are configured to fold across the tissue collector to protect the tissue samples as the tissue collector is moved into the distal lumen opening of the cannula.

4. The apparatus of claim 2 wherein the longitudinally extending gap has a longitudinal gap length, and the bristles have a bristle length extending from the shaft, and the longitudinal gap length and the bristle length are configured to be the same.

5. The apparatus of claim 1 wherein a diameter of the proximal portion of bristles and the distal portion of bristles extending cylindrically from the shaft is greater than the distal lumen opening of the flexible cannula.

6. The apparatus of claim 1 wherein when the brush is retracted, the distal end of the cannula is configured to move at least a portion of the tissue sample from the folding bristles and into the tissue collector.

7. The apparatus of claim 1 wherein the bristles in at least one of the proximal and distal portions of bristles have different material properties than the bristles in the center portion of bristles.

8. The apparatus of claim 1 wherein each bristle in at least one of the proximal and distal portions of bristles deflects differently than each bristle in the center portion of bristles when a same force is applied in the same way to each of the differently deflecting bristles.

9. The apparatus of claim 1 wherein each bristle is in direct contact with each directly adjacent bristle.

10. The apparatus of claim 1 wherein the shaft comprises at least one wire twisted into a helix.

11. The apparatus of claim 1 wherein a second inner lumen extends longitudinally parallel to the first inner lumen from the handle to the distal tip of the flexible cannula, wherein the second inner lumen is operably configured to receive a surgical device therein.

12. A method of collecting and retaining tissue samples from within a patient, said method comprising:
a) providing a cytology brush apparatus having a longitudinal axis and a hollow flexible cannula extending along the longitudinal axis with a longitudinally movable cytology brush extending from a distal end of the hollow flexible cannula, the cytology brush comprising:
i) a proximal bristle portion,
ii) a distal bristle portion,
iii) a center bristle portion between the proximal bristle portion and the distal bristle portion, and
iv) a first tissue collector between the proximal bristle portion and the distal bristle portion;
wherein the proximal portion and distal portion of bristles are stiff bristles for abrading tissue samples from the surgical site, and center portion of bristles are soft bristles for collecting tissue samples abraded from the surgical site;
further wherein the center bristle portion has a length along the longitudinal axis longer than either a length of the proximal bristle portion or a length of the distal bristle portion along the longitudinal axis;
b) collecting tissue samples within the bristles and the first tissue collector of the cytology brush at a surgical site within the patient;
c) drawing the extended cytology brush and collected tissue samples into the hollow flexible cannula;
d) retaining the tissue sample collected within the first tissue collector by folding bristles across the first tissue collector as the extended cytology brush and collected tissue samples are drawn into the hollow flexible cannula.

13. The method of claim 12 further comprising a step of encompassing the cytology brush with the cannula to protect the tissue sample from contamination after the step of folding the proximal brush portion across the tissue sample with the hollow flexible cannula.

14. The method of claim 12 wherein at least one of the proximal bristle portion and the distal bristle portion are further configured to be more abrasive than the center bristle portion to abrade cells from tissue.

15. An apparatus for the collection and retention of tissue samples from within a patient, said apparatus comprising:
a handle;
a flexible cannula extending distally from the handle to a distal end of the cannula; and
a brush assembly movable in and out of the distal end of the cannula by actuation of the handle, the brush comprising:
a shaft extending longitudinally through the cannula, and from the handle to the brush;
a proximal brush portion having a first axial length and comprising an array of bristles extending from the shaft;
a central brush portion located distal to the proximal brush portion and having a second axial length and comprising a cylindrical array of bristles extending from the shaft;
a distal brush portion located distal to the central brush portion and having a third axial length and comprising a cylindrical array of extending from the shaft;
a first longitudinal gap between the proximal brush portion and the central brush portion; and
a second longitudinal gap between the central brush portion and the distal brush portion;
wherein the proximal portion of bristles and distal portion of bristles are stiff bristles for abrading tissue samples from the surgical site, and the center portion of bristles are soft bristles for collecting tissue samples abraded from the surgical site;
further wherein the second axial length is longer than the first axial length and longer than the third axial length.

16. The apparatus of claim 15, wherein the center brush portion comprises bristles having a length equal to an axial length of the first longitudinal gap.

17. The apparatus of claim 15, wherein the center brush portion comprises bristles having a length equal to an axial length of the second longitudinal gap.

18. The apparatus of claim 15, wherein the center brush portion comprises bristles having a length equal to an axial length of the first longitudinal gap and an axial length of the second longitudinal gap.

* * * * *

UNITED STATES PATENT AND TRADEMARK OFFICE
CERTIFICATE OF CORRECTION

PATENT NO. : 8,968,213 B2
APPLICATION NO. : 13/276028
DATED : March 3, 2015
INVENTOR(S) : Eric Roush et al.

Page 1 of 1

It is certified that error appears in the above-identified patent and that said Letters Patent is hereby corrected as shown below:

Title page, item 75 should read as follows

Inventors: Eric Roush, Cleveland Heights, OH (US); Christopher J. Kaye, Concord, OH (US); Sonya Snyder, Chardon, OH (US)

Signed and Sealed this
Third Day of November, 2015

Michelle K. Lee
*Director of the United States Patent and Trademark Office*